United States Patent
Miquel et al.

(10) Patent No.: US 9,827,104 B2
(45) Date of Patent: Nov. 28, 2017

(54) METHOD OF MACHINING A WORKPIECE INTO A DESIRED PATIENT SPECIFIC OBJECT

(71) Applicant: LABORATOIRES BODYCAD INC., Quebec (CA)

(72) Inventors: Florent Miquel, Quebec (CA); Philippe Myrand-Lapointe, Quebec (CA)

(73) Assignee: LABORATOIRES BODYCAD INC., Québec (CA)

( * ) Notice: Subject to any disclaimer, the term of this patent is extended or adjusted under 35 U.S.C. 154(b) by 410 days.

(21) Appl. No.: 14/409,216

(22) PCT Filed: Jun. 27, 2013

(86) PCT No.: PCT/CA2013/000604
§ 371 (c)(1),
(2) Date: Dec. 18, 2014

(87) PCT Pub. No.: WO2014/000091
PCT Pub. Date: Jan. 3, 2014

(65) Prior Publication Data
US 2015/0164644 A1    Jun. 18, 2015

Related U.S. Application Data

(60) Provisional application No. 61/664,923, filed on Jun. 27, 2012.

(51) Int. Cl.
*A61F 2/30* (2006.01)
*A61F 2/32* (2006.01)

(52) U.S. Cl.
CPC ............ *A61F 2/30942* (2013.01); *A61F 2/32* (2013.01); *A61F 2002/3096* (2013.01);
(Continued)

(58) Field of Classification Search
CPC ......... Y10T 29/49995; Y10T 29/49998; Y10T 409/301792; B25B 11/00; B25B 1/08;
(Continued)

(56) References Cited

U.S. PATENT DOCUMENTS 4,936,862 A    6/1990 Walker et al.
5,150,304 A    9/1992 Berchem et al.
(Continued)

OTHER PUBLICATIONS

Binder, William J.; "Custom-Designed Facial Implants", Facial Plastic Surgery Clinics of North America, vol. 16, pp. 133-146, 2008.
(Continued)

*Primary Examiner* — Jermie Cozart
(74) *Attorney, Agent, or Firm* — Marshall, Gerstein & Borun LLP

(57) ABSTRACT

There is provided a device for supporting an object during machining thereof, the object having a first object surface having a patient-specific configuration and a second object surface opposite the first object surface. The device comprises a support member adapted to support the object, the support member having a support surface shaped using patient-specific modeling and configured to matingly engage at least a portion of the first object surface for exposing the second object surface for machining thereof.

9 Claims, 11 Drawing Sheets

(52) U.S. Cl.
CPC ............ *A61F 2002/30948* (2013.01); *Y10T 29/49995* (2015.01); *Y10T 29/49998* (2015.01); *Y10T 409/30868* (2015.01); *Y10T 409/301792* (2015.01); *Y10T 409/303752* (2015.01)

(58) Field of Classification Search
CPC . B25B 5/00; B25B 1/00; B25B 1/2494; B23P 13/02; A61F 2/30942; A61F 2/32; A61F 2002/30948
See application file for complete search history.

(56) References Cited

U.S. PATENT DOCUMENTS

| | | | |
|---|---|---|---|
| 5,184,306 | A | 2/1993 | Erdman et al. |
| 5,677,855 | A | 10/1997 | Skeeters et al. |
| 5,798,924 | A | 8/1998 | Eufinger et al. |
| 6,832,877 | B2 | 12/2004 | Hamada |
| 7,474,932 | B2 | 1/2009 | Geng |
| 8,016,644 | B2 | 9/2011 | Curodeau et al. |
| 2003/0123943 | A1 | 7/2003 | Hamada |
| 2003/0125189 | A1 | 7/2003 | Castro et al. |
| 2005/0065628 | A1 | 3/2005 | Roose |
| 2006/0094951 | A1 | 5/2006 | Dean et al. |
| 2007/0118243 | A1 | 5/2007 | Schroeder et al. |
| 2008/0081539 | A1 | 4/2008 | Ernsberger |
| 2008/0228303 | A1 | 9/2008 | Schmitt |
| 2009/0017732 | A1 | 1/2009 | Curodeau et al. |
| 2009/0157185 | A1 | 6/2009 | Kim |
| 2010/0203478 | A1 | 8/2010 | Rubbert |
| 2010/0268363 | A1 | 10/2010 | Karim et al. |
| 2010/0285429 | A1 | 11/2010 | Karim et al. |
| 2011/0266265 | A1 | 11/2011 | Lang |

OTHER PUBLICATIONS

Huang et al.; "Fabricating auricular prostheses based on rapid prototyping and the FreeForm modelling system", Institute of Life Quality via Mechanical Enineer, P.R. China, 2004, vol. 24, pp. 873-878.

Patel, N.; "Integrating Three-Dimensional Digital Technologies for Comprehensive Implant Dentistry", The Journal of the American Dental Association, vol. 141, pp. 20S-24S, Jun. 2010.

Smith et al.; "The use of CAD/CAM technology in prosthetics and orthotics—Current clinical models and a view to the future", University of Washington; Prosthetics Research Study, and the Amputee Coalition of America, Seattle, WA, Journal of Rehabilitation Research and Development, vol. 38, No. 3, May/Jun. 2001, pp. 327-334.

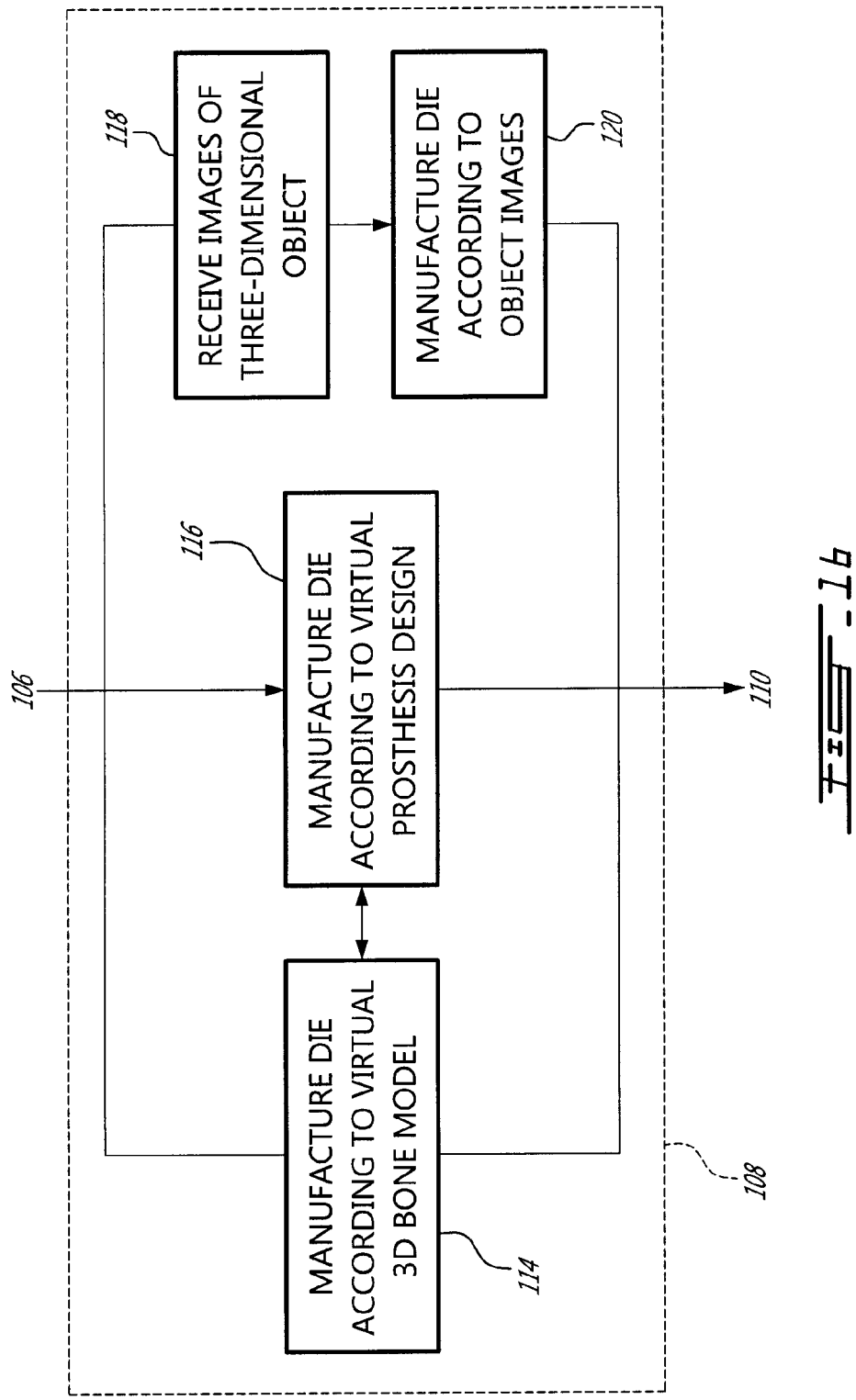

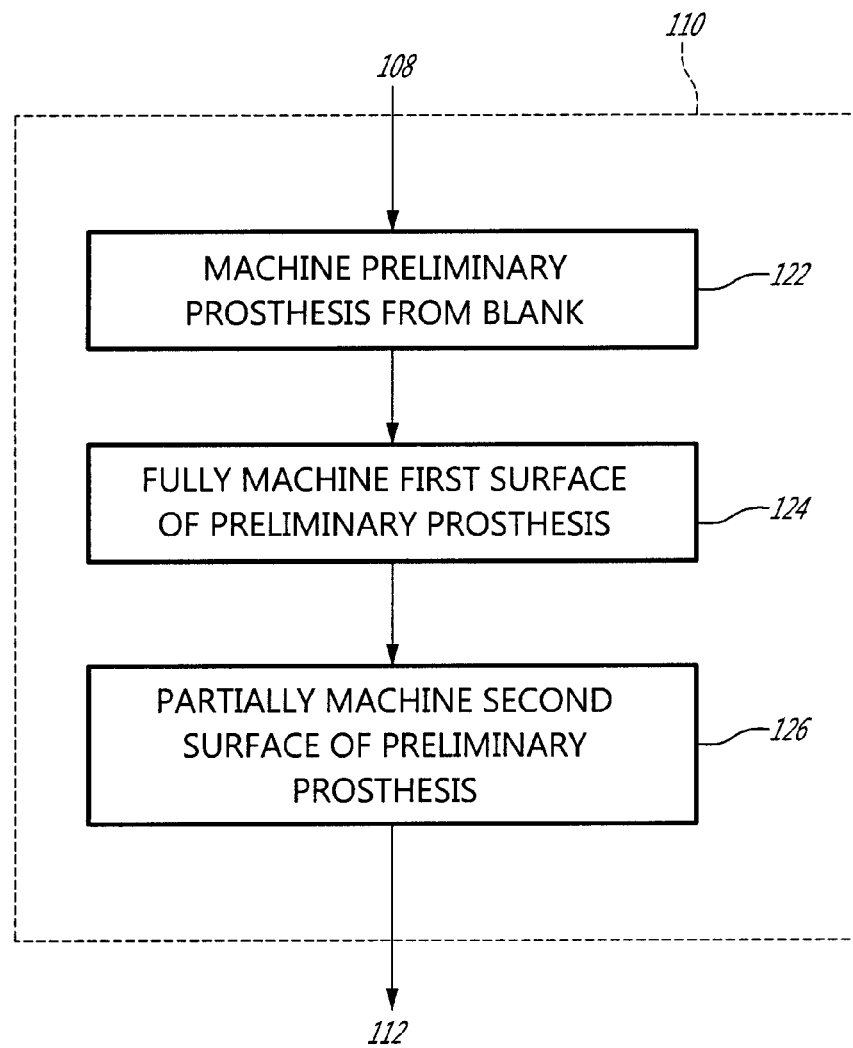

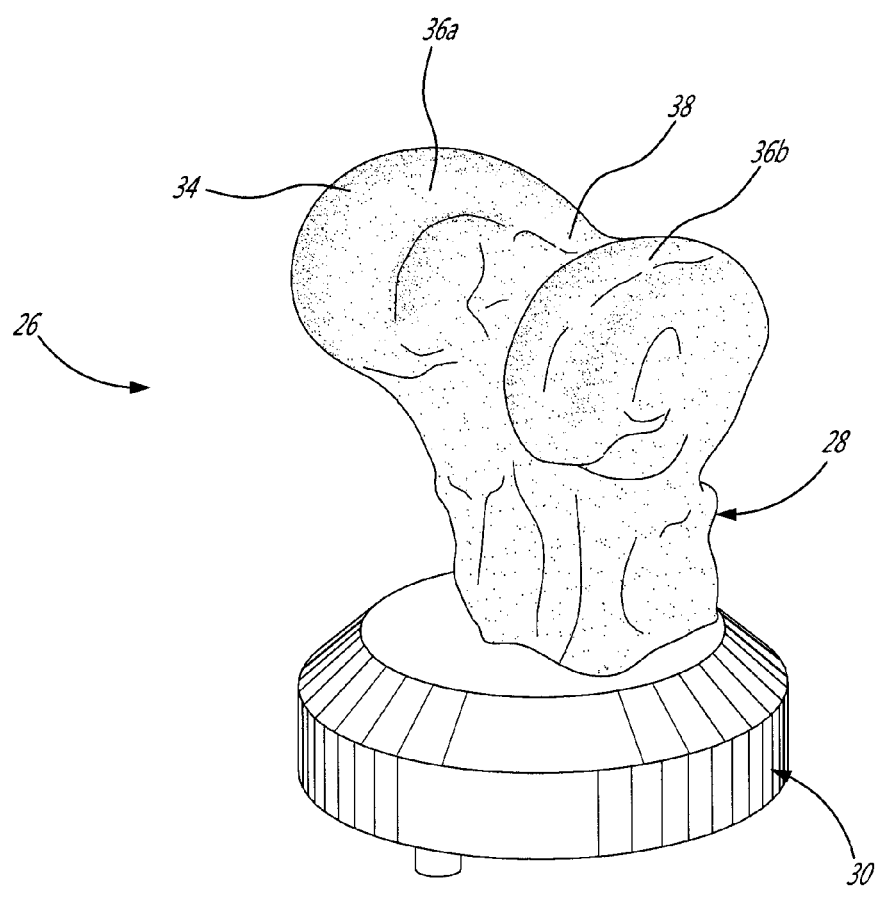

METHOD OF MACHINING A WORKPIECE INTO A DESIRED PATIENT SPECIFIC OBJECT

CROSS-REFERENCE TO RELATED APPLICATIONS

This patent application claims priority of US provisional Application Ser. No. 61/664,923, filed on Jun. 27, 2012.

TECHNICAL FIELD

The present invention relates to the field of object machining, and, more particularly, to methods for holding an object in place during machining.

BACKGROUND OF THE ART

Prostheses may be used to replace missing body parts or repair damaged articular joints. Each patient's anatomy being different, it may be desirable to design patient-specific prostheses, which are adapted to fit each patient's unique anatomical features. Using such prostheses may indeed improve the outcome of the surgical procedure.

Prosthetic components are usually machined to have a surface adapted to mate with a resected bone surface. Attachment pins may further be provided on the surface of the prosthesis component for securing the latter to the bone. During the machining process, such pins may also be used to secure the prosthesis component being machined to a support, such as a vise. However, when dealing with patient-specific prosthesis components, the prosthesis surface is typically customized to fit the patient's anatomy. As such, the mating of the prosthesis with the resected bone surface is achieved by the unique form of the prosthesis surface and no attachment pins may be used. It may therefore prove difficult to use conventional supports to secure patient-specific prosthesis components during machining thereof.

There is therefore a need for an improved device and method for holding a machined object, such as a prosthesis, in place during machining thereof.

SUMMARY

In accordance with a first broad aspect, there is provided a device for supporting an object during machining thereof, the object having a first object surface having a patient-specific configuration and a second object surface opposite the first object surface. The device comprises a support member adapted to support the object, the support member having a support surface shaped using patient-specific modeling and configured to matingly engage at least a portion of the first object surface for exposing the second object surface for machining thereof.

In accordance with a second broad aspect, there is provided a method of machining a workpiece into a desired patient-specific object having a first patient-specific surface and a second patient-specific surface opposite the first patient-specific surface. The method comprises receiving a digital object representation representative of the desired patient-specific object, machining, in accordance with the received digital object representation, the workpiece into a partially machined object, the partially machined object having a first object surface replicating the first patient-specific surface and a second object surface opposite the first surface, securing the partially machined object to a support member, the support member having a support surface shaped using patient-specific modeling and configured to matingly engage at least a portion of the first object surface for exposing the second object surface, and machining, in accordance with the received digital object representation, the exposed second object surface to replicate the second patient-specific surface.

In accordance with a third broad aspect, there is provided an apparatus for machining an object having a first object surface and a second object surface opposite the first object surface, the first object surface having a patient-specific configuration. The apparatus comprises a machine frame, a cutting tool mounted to the machine frame, and a support member for supporting the object, the support member having a support surface shaped using patient-specific modeling and configured to matingly engage at least a portion of the first object surface for exposing the second object surface to the cutting tool.

BRIEF DESCRIPTION OF THE DRAWINGS

Further features and advantages of the present invention will become apparent from the following detailed description, taken in combination with the appended drawings, in which:

FIG. 1b is a flowchart of the step of FIG. 1a of manufacturing a custom die;

FIG. 1c is a flowchart of the step of FIG. 1a of partially machining a prosthesis;

FIG. 3b is a side detailed view of the inner surface of the prosthesis of FIG. 3a;

FIG. 3c is a front detailed view of the inner and outer surface of the prosthesis of FIG. 3a;

FIG. 5 is a perspective view of the custom die of FIG. 4 without the preliminary prosthesis supported thereon;

FIG. 6b is a perspective view of the custom die of FIG. 6a with a finished prosthesis supported thereon.

It will be noted that throughout the appended drawings, like features are identified by like reference numerals.

DETAILED DESCRIPTION

Figure 1A:
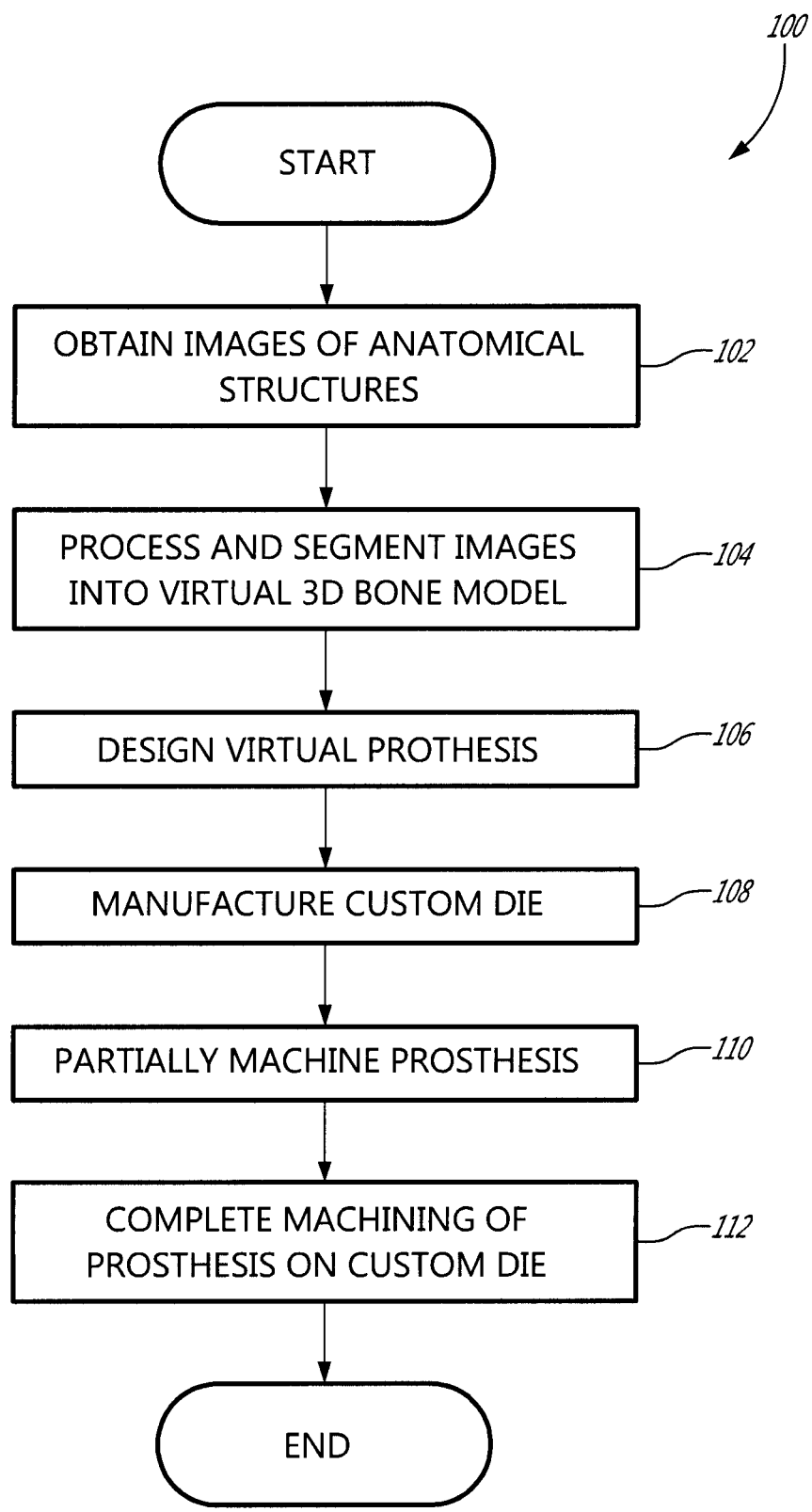
FIG. 1a is a flowchart of a method for manufacturing a patient-specific object, in accordance with an illustrative embodiment of the present invention.

Referring to FIG. 1a, a computer-aided method 100 for manufacturing a patient-specific object will now be described. It should be understood that, although the description below refers to the manufacturing of a patient-specific prosthesis, other patient-specific objects, such as cutting blocks, surgical tools, or the like, which may interact or be mated with anatomical structures of an individual, e.g. a patient, during a surgical procedure or the like, may apply.

The method 100 comprises obtaining at step 102 images of anatomical structures, which refers to acquiring image data of the anatomical region of the individual's body where the prosthesis is to be implanted. Such anatomical region may for example comprise the hip, knee, and ankle regions when total knee replacement surgery is concerned. Although the method 100 is described herein with reference to a knee, it should be understood that the method 100 may apply to other articular joints, such as an elbow, shoulder, wrist, or hip. It should also be understood that the method may apply to prostheses other than articular joint repair prostheses. For instance, facial or dental prostheses may apply.

The images may be obtained from scans generated using Magnetic Resonance Imaging (MRI), Computed Tomography (CT), ultrasound, x-ray technology, optical coherence tomography, or the like. Such images may be provided by a user, such as a medical technician, a surgeon, or a treating physician, via a suitable communication means to a computer system (not shown) adapted to process the method 100. For this purpose, the user may electronically provide the scans of the individual's anatomy to the computer system via electronic mail, a Picture Archiving and Communication System (PACS) server, a website, or the like. The captured images may further be provided in various known formats, such as Digital Imaging and Communications in Medicine (DICOM), for handling, storing, printing, and transmitting information via PACS. Other exemplary formats are GE SIGNA Horizon LX, Siemens Magnatom Vision, SMIS MRD/SUR, and GE MR SIGNA 3/5 formats.

Once the images of the individual's anatomy have been obtained at step 102, they may be processed and segmented at step 104. Indeed, as images may be acquired along one or more planes throughout the body part, such as sagittal, coronal, and transverse, as well as multiple orientations, the data may be combined or merged during processing. Image segmentation may further be performed in order to extract from the images information related to the individual's damaged knee joint, such as the mechanical leg axis or the size of the tibial plateau and femoral head. A virtual three-dimensional (3D) representation of the damaged knee joint may then be created from the segmented images. It should be understood that a virtual two dimensional (2D) bone model of the individual's damaged knee joint may also be provided. The selection of the type of bone model to be generated, namely 2D or 3D, is illustratively made according to user preferences, such as technical capabilities associated with a device the user employs to interact with the computer system.

Using such a virtual 3D bone model as well as additional design parameters and patient-related information, which may be provided by the user, a patient-specific prosthesis adapted to fit the patient's unique anatomy may be virtually designed at step 106 using patient-specific modeling. Using such modeling, the patient-specific prosthesis (or other suitable patient-specific object) can be created so as to comprise one or more surfaces adapted to interact or be precisely mated with one or more surfaces of the patient's unique anatomical structures. The patient-specific modeling can be used to manufacture objects, e.g. the patient-specific prosthesis or the custom die, having surfaces that conform to one or more surfaces having a patient-specific configuration that corresponds to unique anatomical structures of an individual.

A custom die may then be manufactured at step 108 using patient-specific modeling. Such a die may be used for supporting the prosthesis during machining thereof, as will be described further below. The prosthesis may indeed first be partially machined at step 110 using a suitable device, such as a milling machine, or the like, from a blank workpiece. The machining may then be completed at step 112 with the prosthesis being supported on the manufactured custom die. It should be understood that steps 108 and 110 may be interchanged as the prosthesis may be partially machined prior to manufacturing the custom die. Also, the step 106 of virtually designing the prosthesis may be done after the custom die is manufactured 108.

Computer-aided machining (CAM) may be used for performing free-form machining of the prosthesis at steps 110 and 112. For this purpose, machining parameters related for example to the prosthesis material, cutting tools, and cutting operations, may be defined. A machining trajectory used for producing the prosthesis may then be generated. A computer numerical control (CNC) code specifying the tool paths as well as any additional information useful for avoiding machine collisions may also be generated and sent to machining tools over a suitable communication link.

Referring to FIG. 1b, the step 108 of manufacturing the custom die may comprise at least one of manufacturing the die according to the virtual 3D bone model at step 114 and manufacturing the die according to the virtual prosthesis design (e.g. the digital representation of the prosthesis) at step 116. The step 108 may further comprise receiving at step 118 images of a three-dimensional object, such as a second patient-specific prosthesis that the desired prosthesis (to be machined at steps 110 and 112 of FIG. 1a) will be mated with when implanted in the patient's body. The die may then be manufactured at step 120 according to the received object images. The die may be manufactured at any one of steps 114, 116, and 120 by casting, milling, molding, rapid prototyping, or any other suitable method. The die may be manufactured by adding material to or removing material from a workpiece.

It should be understood that, at step 114, the die may be manufactured on the basis of part or the whole of the virtual 3D bone model. For instance, when the prosthesis to be machined is a femoral component that is to be positioned on a femur, the die may be manufactured according to only the femoral part of the virtual 3D bone model. Similarly, if a tibial prosthesis component is being machined for placement on a tibia, the die may be manufactured according to only the tibial part of the virtual 3D bone model. Also, when the machined prosthesis is to be spaced from the bone when implanted, the die may be manufactured taking this spacing into account. In particular, the die may be manufactured so that the outer surface thereof is offset from the actual bone surface by the desired spacing. In this case, the thus manufactured die is not an exact replica of the individual's bone but an offset representation thereof. This can ensure that, although the prosthesis is to be spaced from the bone surface when implanted, the prosthesis is supported on the die without any spacing between the supported prosthesis surface and the die's supporting surface. As such, the manufactured die illustratively conforms to the bone model by either completely corresponding thereto (e.g. being a replica of the bone surface) or being somewhat offset therefrom.

It should also be understood that either an internal or an external surface of the prosthesis partially machined at step 106 may need to be subsequently reworked. As such, either the internal or the external surface of the partially machined prosthesis will be supported on the custom die during machining. For instance, in cases where the internal surface of the prosthesis partially machined at step 106 is to be subsequently reworked, the external surface of the partially machined prosthesis may be supported on the custom die. Accordingly and as will be discussed further below, depending on the prosthesis surface to be supported on the die, the latter may be machined to have a support surface that conforms to (e.g. corresponds to or otherwise cooperates with) the shape of at least a portion of the prosthesis surface that will be supported on the die rather than conforming to a shape of a bone surface the prosthesis surface is to be mated with. This may then enable to provide better support of the prosthesis component on the die. Consequently, in such cases, the die may not be manufactured according to the virtual 3D bone model at step 114. Instead, the die may be manufactured at step 116 on the basis of the virtual design of the prosthesis and using patient-specific modeling. It should be understood that the die may also be manufactured on the basis of both the virtual prosthesis design and the 3D bone model.

Moreover, depending on the type of prosthesis to be manufactured, the reworked internal or external surface of the prosthesis, once implanted in the patient's body, may not mate with any of the individual's bones but rather with a second machined object, e.g. a patient-specific prosthesis. This is the case for example of a femoral component whose external surface may mate with a mating surface of a tibial prosthetic component rather than with the tibia. As such, the custom die may be manufactured at step 120 as an object having a supporting surface, which corresponds to a mating surface of a machined object the prosthesis will be mating with when implanted. As such, the supporting surface may still be adapted to matingly engage the surface of the partially machined prosthesis that is being supported, e.g. the external surface, while not being manufactured to be a representation of a bone of the individual. In this case, the images obtained at step 118 may comprise images of the second machined object, e.g. the patient-specific tibial component, the currently machined object, e.g. the femoral component, is to be mated with. The images illustratively include images of the mating surface of the second machined object. Such images may be obtained using techniques for three-dimensional scanning of objects, e.g. white light, laser dot or line projection, time-of-flight techniques, or the like.

Referring to FIG. 1c, the step 110 of partially machining the prosthesis (according to the virtual design obtained at step 106 of FIG. 1a) illustratively comprises a step 122 of machining the general shape of the prosthesis, i.e. a rough or preliminary prosthesis, from a blank workpiece. A first surface, e.g. the internal surface, of the obtained preliminary prosthesis may then be fully machined at step 124 while a second surface opposite the first surface, e.g. the external surface, may be partially machined at step 126. It may indeed be desirable for the internal surface of the preliminary prosthesis to be fully machined as this internal surface will illustratively be in contact with an outer surface of the die the preliminary prosthesis will be positioned on. The preliminary prosthesis obtained after step 126 illustratively conforms to the shape of the desired prosthesis and has a fully machined first, e.g. internal, surface but has a second, e.g. external, surface, which is not yet fully machined and on which work remains to be done. As discussed above, it should be understood that, if the outer surface of the die is adapted to mate with the external surface of the preliminary prosthesis, the external prosthesis surface may alternatively be fully machined while the internal surface is partially machined.

Figure 1D:
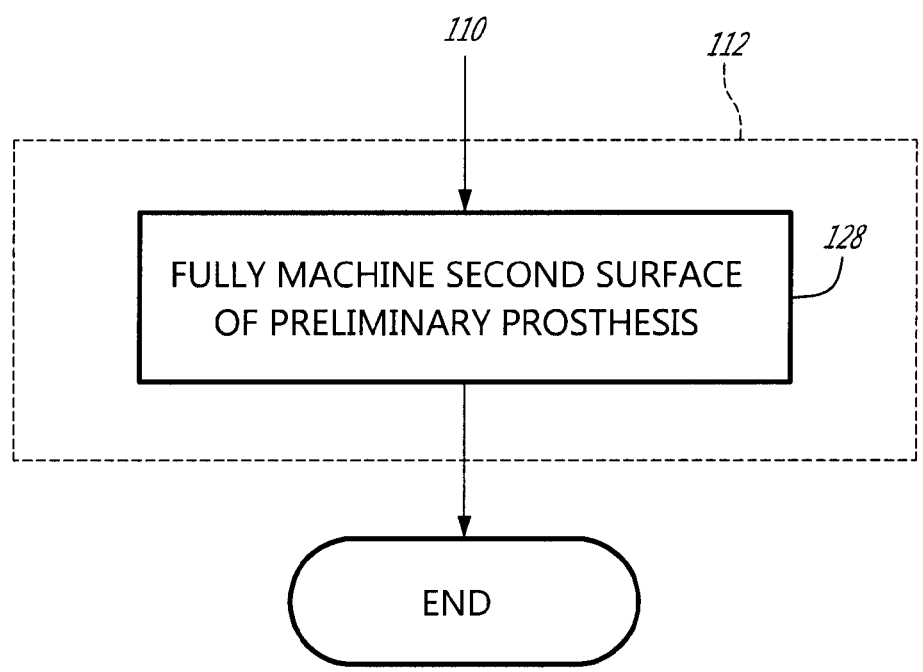
FIG. 1d is a flowchart of the step of FIG. 1a of completing the machining of a prosthesis on a custom die.

Referring to FIG. 1d, the step 112 of completing the machining of the prosthesis on the custom die thus comprises fully machining at step 128 a surface of the preliminary prosthesis, e.g. the external surface, which is opposed to the surface for which machining has already been completed. This may be effected with the preliminary prosthesis supported on a custom die having an outer surface adapted to precisely fit the already machined surface, as will be discussed further below.

Figure 2:
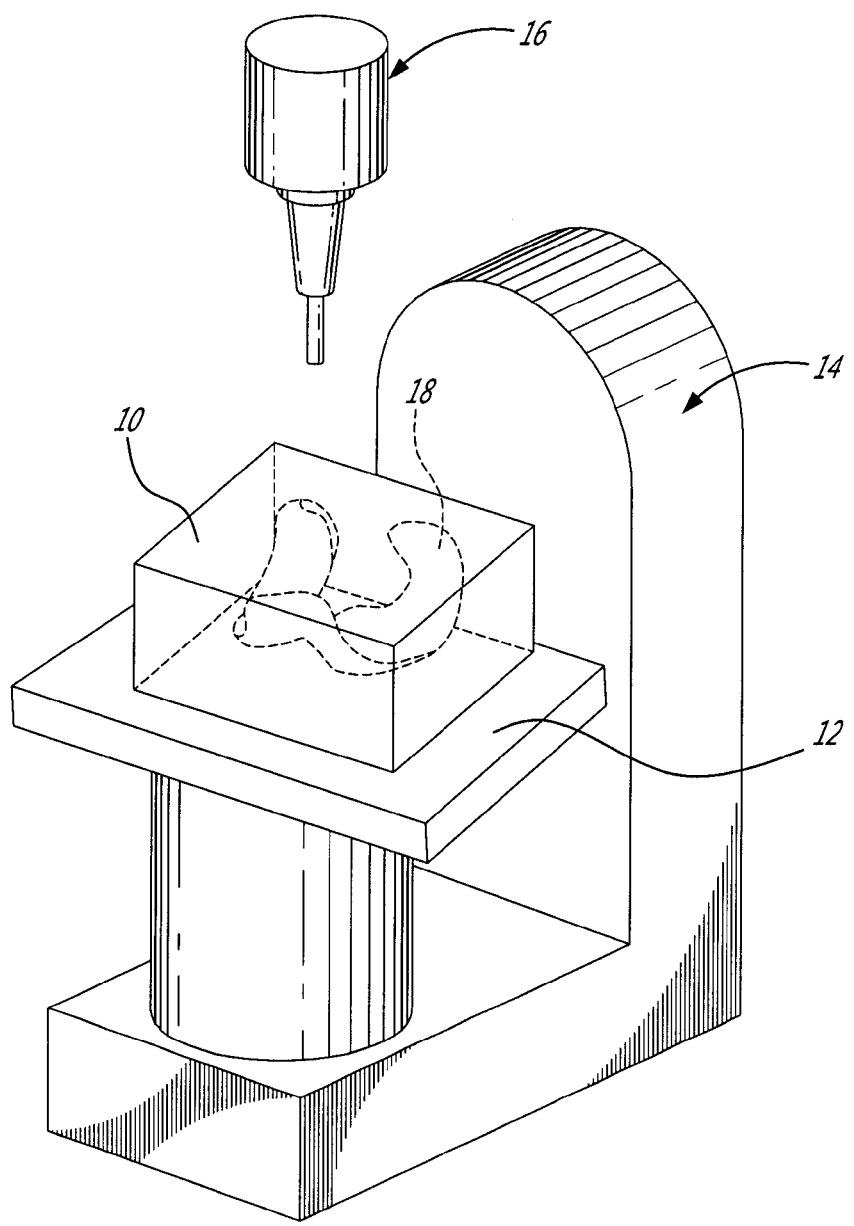
FIG. 2 is a schematic diagram of a workpiece positioned on a milling machine, in accordance with an illustrative embodiment of the present invention.

Referring to FIG. 2, during machining, a blank workpiece 10 may first be positioned on a support frame 12 of a milling machine 14 and retained thereon using clamps or other supports (not shown). A cutting tool 16 coupled to a frame (not shown) of the machine 14 may then remove material from the workpiece 10 to aim at achieving a desired prosthesis 18. The material of the workpiece 10 may comprise any material suitable for biocompatibility, such as a metal alloy, titanium, medical grade stainless steel, tantalum, and ceramics. Although the workpiece 10 has been illustrated as having the shape of a parallelepiped, it should be understood that any other shape, such as a cylinder, may apply. The desired prosthesis 18 is illustratively designed on the basis of images of the individual's anatomical structures obtained at step 102 of the method 100 of FIG. 1a. The thus designed prosthesis 18 may therefore be precisely fitted to the individual's unique anatomical region, thus increasing the outcome of a surgical procedure. The desired prosthesis 18 is illustrated as a femoral component but may be any other prosthesis component, such as a tibial component, as known to those skilled in the art.

Figure 3A:
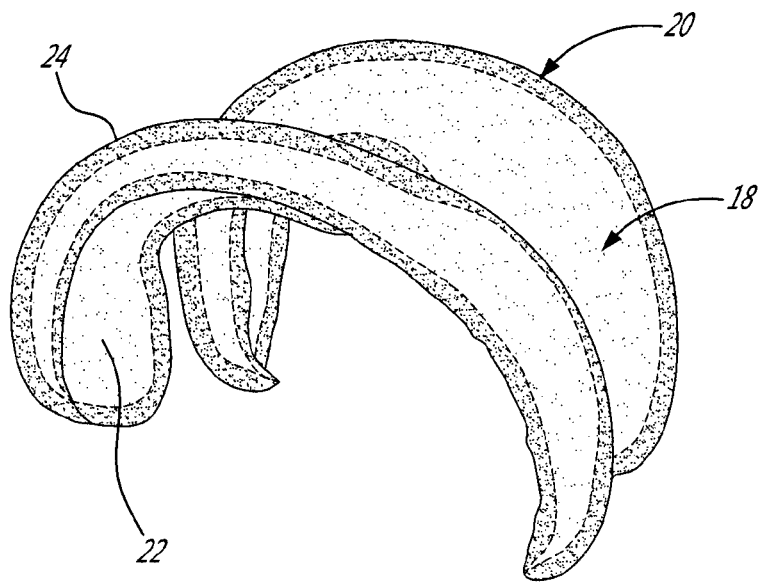
FIG. 3a is a side perspective view of a preliminary prosthesis, in accordance with an illustrative embodiment of the present invention.

Referring to FIG. 3a in addition to FIG. 2, as the cutting tool 16 may only be provided limited access to all faces of the workpiece 10, a preliminary prosthesis 20 rather than the desired prosthesis 18 may be obtained on a first pass or trajectory of the cutting tool 16. The preliminary prosthesis 20 may indeed be a finished product, which is as close as possible to the shape and size of the desired prosthesis 18 but may require additional machining to arrive at the final shape of the desired prosthesis 18. In particular, the cutting tool 16 may not be able to fully machine one or more surfaces of the preliminary prosthesis 20 and this surface or surfaces may then be reworked with more precision using a custom die (not shown) as a support for the preliminary prosthesis 20.

Figure 3B:
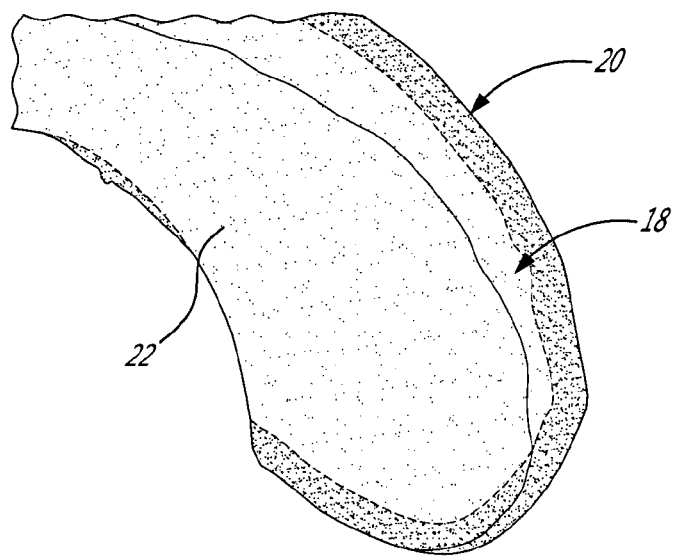
Figure 3C:
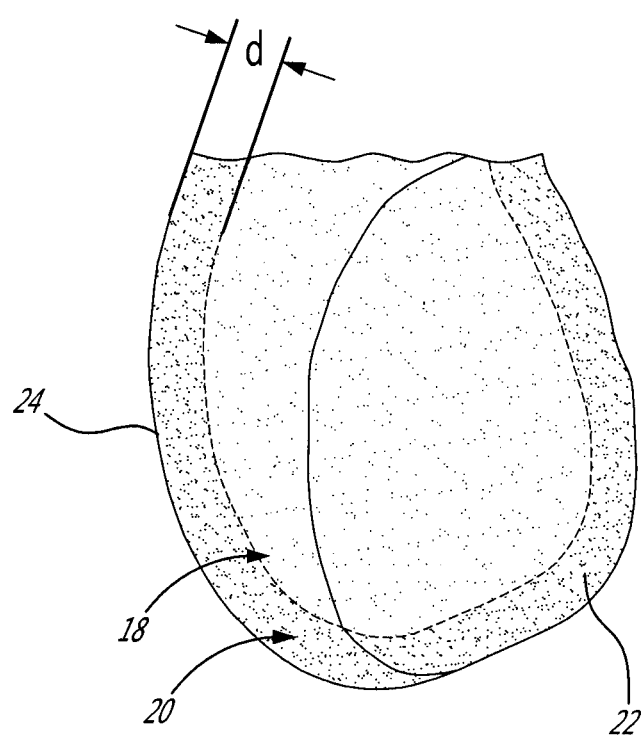

Referring to FIG. 3b and FIG. 3c in addition to FIG. 3a, the preliminary prosthesis 20 may comprise an internal surface 22, which may have been fully machined by the cutting tool 16 so that the internal surface 22 precisely conforms to, i.e. replicates, the internal face (not shown) of the desired prosthesis 18. The preliminary prosthesis 20 may further comprise an external surface 24, which may be partially machined and outlined by the cutting tool 16 with as much precision as possible on the initial trajectory of the cutting tool 16. However, the external surface 24 may need to be reworked by the cutting tool 16 on a supplementary path in order to arrive at the desired final result, i.e. the outer face (not shown) of the desired prosthesis 18. The preliminary prosthesis 20 may indeed be substantially thicker than the desired prosthesis 18 with the external surface 24 of the preliminary prosthesis 20 being illustratively thicker than the outer surface of the desired prosthesis 18 by a distance d. The distance d may be in the range between a few tenth of a millimeter and ten (10) millimeters. It should be understood that the distance d may not be uniform and may vary throughout the external surface 24. It should also be understood that the preliminary prosthesis 20 may have a shape, which is closer to the shape of the workpiece 10 rather than resembling the shape of the desired prosthesis 18 (as illustrated in FIG. 3b and FIG. 3c).

Figure 4:
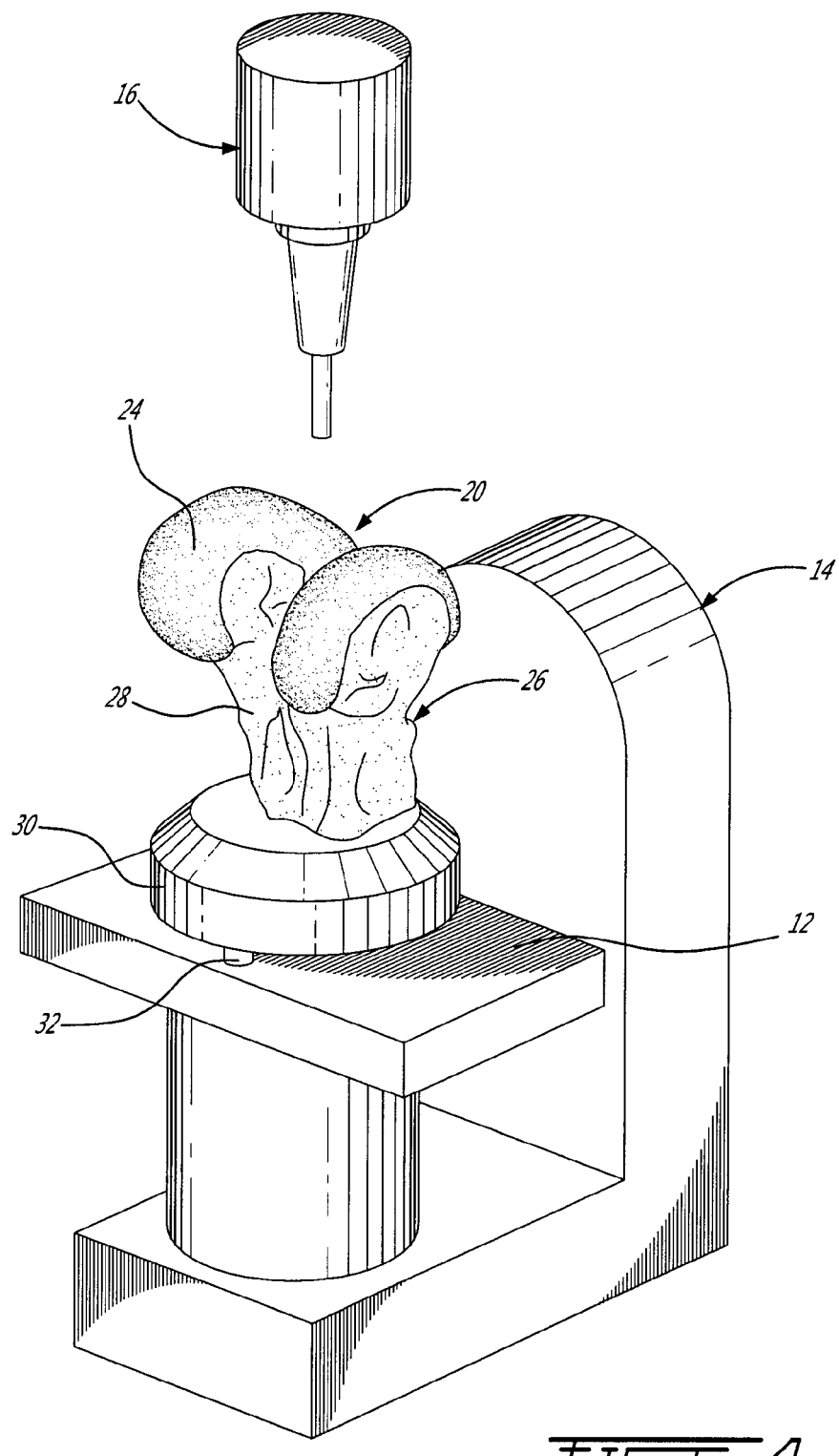
FIG. 4 is a schematic diagram of a custom die, with the preliminary prosthesis of FIG. 3a coupled thereto, positioned on a milling machine.

Referring to FIG. 4, a custom die 26 may be used to support the preliminary prosthesis 20 during reworking thereof. For this purpose, the die 26 and preliminary prosthesis 20 may be positioned on the milling machine 14 enable the cutting tool 16 to remove excess material from the external and exposed surface 24 of the preliminary prosthesis 20. The die 26 illustratively comprises a support member 28 adapted to receive thereon the preliminary prosthesis 20. The support member 28 illustratively extends away from a base member 30 and towards the cutting tool 16 when the die 26 is in position on the milling machine 14. The support member 28 may be attached to the base member 30 using suitable fastening means, such as screws, bolts, rivets, pins, and the like. It should be understood that the support member 28 and the base member 30 may also be machined as a single element, thereby alleviating the need to attach the members 28, 30 to one another. In this manner, with the preliminary prosthesis 20 in place on the support member 28, the cutting tool 16 may be provided access to the external surface 24 for which machining is to be completed. For this purpose, the base member 30 may comprise pegs 32 for securing the base member 30 to the support frame 12 of the milling machine 14. The pegs 32 may be mated with corresponding holes (not shown) provided in the support frame 12, thereby holding the die 26 in place and ensuring stability thereof during the milling process. A support, such as a vise (not shown), may further be coupled to the base member 30 during machining of the preliminary prosthesis 20. It should be understood that other attachment means for securing the base member 30 to the milling machine 14 may apply.

Referring to FIG. 5, the die 26 is illustratively made of plastic, plaster, metal, or any other suitable material known to those skilled in the art. The support member 28 may be manufactured according to the virtual bone model obtained at step 104 of the method 100 described above. As such, the support member 28 may precisely (or closely when a spacing is to be taken into account, as discussed above) conform to the shape of the individual's anatomical structures, and more particularly to the bone(s), to which the desired prosthesis 18 is to be secured for repairing the individual's damaged joint. For example, if the desired prosthesis 18 is a femoral component, as illustrated in FIG. 2, the die 26 illustratively conforms to the shape of the distal end of the patient's femur to which the machined femoral component, and more particularly the internal surface 22 thereof, is to be engaged with. The die 26 may therefore be machined to have an outer surface 34, which conforms to the articular joint to be repaired. In particular, the die 10 may be machined to comprise representations of anatomical structures of the patient's femur, such as machined femoral condyles 36a, 36b and a machined patellofemoral groove 38. In this manner, the outer surface 34 of the die 26 may conform to the patient's actual articular joint surface and may therefore be adapted to precisely mate with the internal surface 22 of the preliminary prosthesis 20 to be coupled thereto.

Still, depending on the type of the desired prosthesis 18, the support member 28 may not conform to the shape of the individual's bones, as discussed above. Instead, the support member 28 may conform to the shape of another machined object (not shown), such as a tibial prosthetic component, the desired prosthesis 18 is to be mated with. Also, machining of the support member 28 may depend on the surface of the preliminary prosthesis 20 that is to be supported on the support member 28. Indeed, as discussed above, the external surface 24 may be fully machined while the internal surface 22 is partially machined. As such, the external surface 24 may be supported on the die 26 for reworking the internal surface 22. In the case where a femoral prosthesis component is being machined, as illustrated, the preliminary surface 24 may not be properly supported on the die 26 if the latter is manufactured such that the outer surface 34 conforms to the surface of the individual's tibia that the preliminary prosthesis 20, once turned into the desired prosthesis 18, will be mated with. Indeed, due to the arcuate shape of the femoral prosthesis component, the substantially planar shape of the tibial surface may not prove suitable for preventing movement of the preliminary prosthesis 20 relative to the die 26. As such, when supported on the die 26, the preliminary prosthesis 20 may not be held in place during machining. In order to avoid such an issue, the die 26 may be manufactured on the basis of the virtual prosthesis design such that the outer surface 34 corresponds to at least a portion of the external surface 24 that is to be supported on the die 26. This may then ensure adequate mating of the external surface 24 with the outer surface 34, and accordingly adequate support of the preliminary prosthesis 20 on the die.

In one embodiment, the outer surface 34 may be shaped and sized to precisely conform to the shape and size of the external surface 24. In other embodiments, the outer surface 34 may be shaped and sized to conform to the shape and size of a portion of the external surface 24. It is desirable for such a portion of the external surface 24 to be sufficient to securely hold the preliminary prosthesis 20 in place relative to the die 26 when the outer surface 34 is mated with the portion of the external surface 24. It should be understood that the portion of the external surface 24 may vary according to the desired prosthesis 18 to be machined. 36. It should also be understood that this may also apply when the internal surface 22 of the preliminary prosthesis 20 is to be supported on the die 26. Indeed, in this case, the outer surface 34 may be manufactured so as to conform to at least a portion of the internal surface 22 rather than being manufactured to conform to the articular joint (e.g. bone surface) or mating surface the preliminary prosthesis 20 is to be mated with, as discussed above.

Figure 6A:
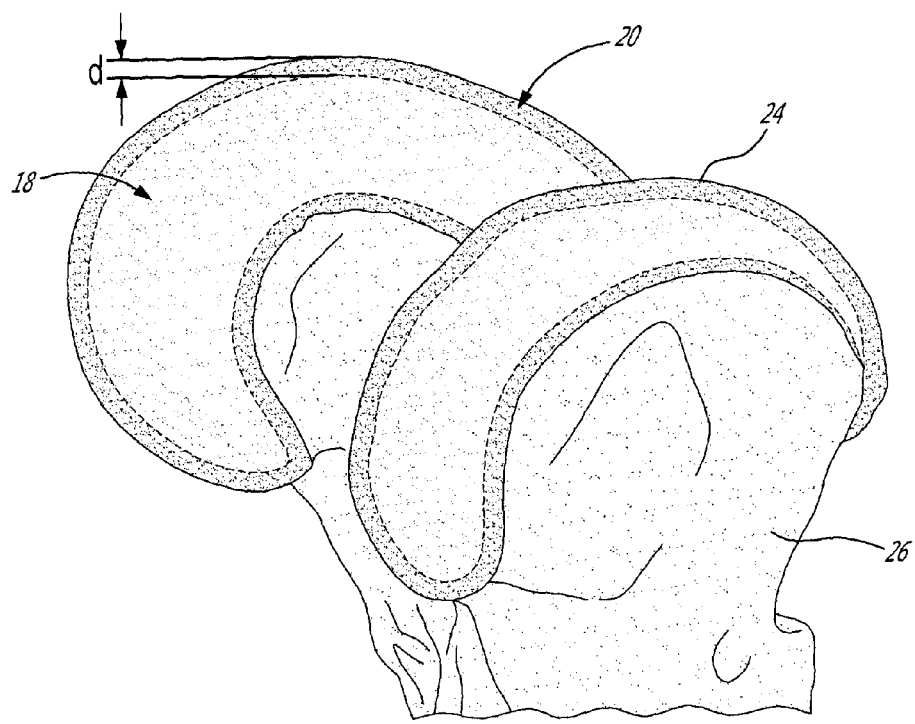
FIG. 6a is a perspective view of the custom die of FIG. 4 with the preliminary prosthesis supported thereon.
Figure 8B:
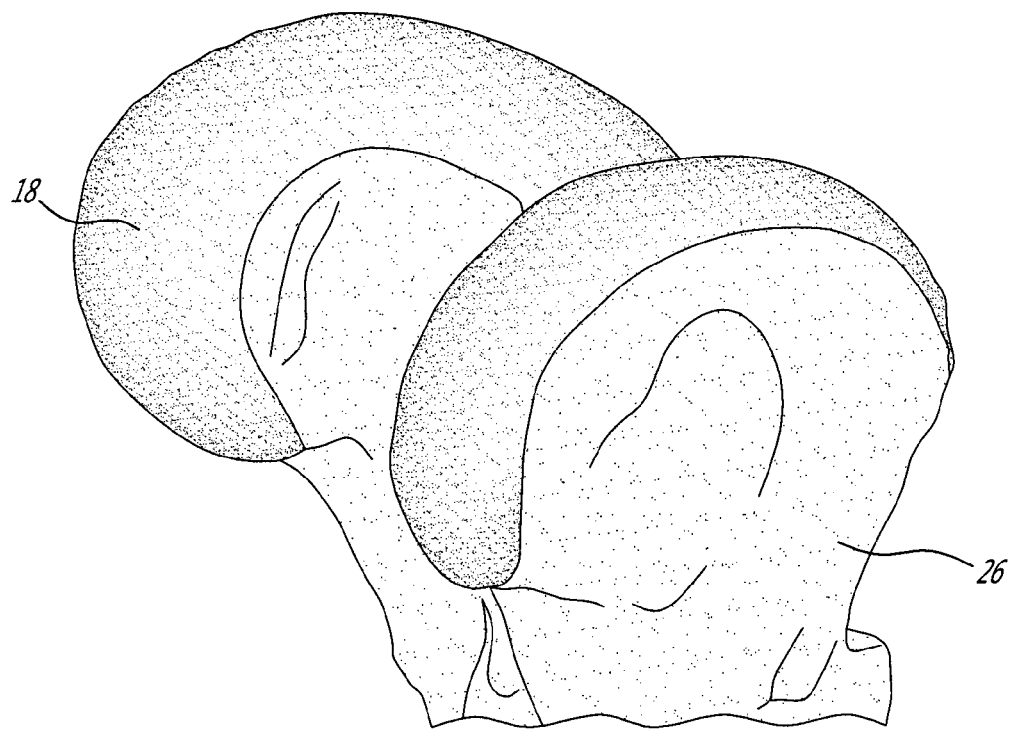

Referring to FIG. 6a and FIG. 6b, machining of the external surface 24 of the preliminary prosthesis 20 may be performed with the latter held in place on the die 26. In particular, the preliminary prosthesis 20 may be positioned on the die 26 with the internal surface 22 (or alternatively the external surface 24) of the preliminary prosthesis 20 matingly engaged with the outer surface 34 of the die 26. By machining the external surface 24 (or alternatively the internal surface 22) using the cutting tool 16, material may be removed, thereby reducing the thickness d of the external surface 24 (or alternatively the internal surface 22) in order to arrive at the desired prosthesis 18. Once the preliminary prosthesis 20 has been machined to achieve the desired prosthesis 18, the latter may then be removed from the die 26 for shipping to a desired location.

Using the approach described herein, precise machining of a prosthesis component or any other object known to those skilled in the art, may be achieved. In particular, reworking of the object may be facilitated and the finished product may therefore be closer to the designed product. Better results may in turn be achieved.

The embodiments of the invention described above are intended to be exemplary only. The scope of the invention is therefore intended to be limited solely by the scope of the appended claims.

The invention claimed is:

1. A method of machining a workpiece into a desired patient-specific object having a first patient-specific surface and a second patient-specific surface opposite the first patient-specific surface, the method comprising:

receiving a digital object representation representative of the desired patient-specific object;

machining, in accordance with the received digital object representation, the workpiece into a partially machined object, the partially machined object having a first object surface replicating the first patient-specific surface and a second object surface opposite the first surface;

securing the partially machined object to a support member, the support member having a support surface shaped using patient-specific modeling and configured to matingly engage at least a portion of the first object surface for exposing the second object surface; and machining, in accordance with the received digital object representation, the exposed second object surface to replicate the second patient-specific surface.

2. The method of claim 1, further comprising manufacturing the support member on the basis of the received digital object representation such that the support surface corresponds to at least the portion of the first patient-specific surface.

3. The method of claim 1, wherein the first patient-specific surface is adapted to matingly engage a mating surface of at least one body, the method further comprising receiving a digital body representation representative of the at least one body and manufacturing the support member on the basis of the received digital body representation such that the support surface corresponds to the mating surface of the at least one body.

4. The method of claim 3, wherein manufacturing the support member on the basis of the received digital body representation comprises manufacturing the support surface to completely correspond to the mating surface.

5. The method of claim 3, wherein manufacturing the support member on the basis of the received digital body representation comprises manufacturing the support surface to be an offset representation of the mating surface.

6. The method of claim 3, wherein the at least one body is at least one bone and receiving the digital body representation comprises receiving a virtual bone model of the at least one bone.

7. The method of claim 3, wherein the at least one body is a machined patient-specific object and receiving the digital body representation comprises receiving at least one image of the machined patient-specific object.

8. The method of claim 1, wherein machining the workpiece into a partially machined object further comprises fully machining one of the first object surface and the second object surface resulting in a fully machined object surface for which at least a portion thereof engages with the support surface of the support member.

9. The method of claim 1, further comprising reworking one of the first object surface and the second object surface, the first object surface or the second object surface being received by the support surface of the support member, the support member extending away from a base member and towards a cutting tool of a milling machine adapted to machine the object with the base member secured to the milling machine.

* * * * *